US010865395B2

United States Patent
Yang et al.

(10) Patent No.: US 10,865,395 B2
(45) Date of Patent: *Dec. 15, 2020

(54) THERMOSTABLE TAGATOSE-6-PHOSPHATE PHOSPHATASE AND A METHOD FOR PRODUCING TAGATOSE USING THE SAME

(71) Applicant: CJ CHEILJEDANG CORPORATION, Seoul (KR)

(72) Inventors: Sungjae Yang, Suwon-si (KR); Hyun Kug Cho, Seoul (KR); Young Mi Lee, Suwon-si (KR); Seong Bo Kim, Seongnam-si (KR); Seong Jun Cho, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/314,250

(22) PCT Filed: Jun. 30, 2017

(86) PCT No.: PCT/KR2017/006988
§ 371 (c)(1),
(2) Date: Dec. 28, 2018

(87) PCT Pub. No.: WO2018/004310
PCT Pub. Date: Jan. 4, 2018

(65) Prior Publication Data
US 2019/0203189 A1    Jul. 4, 2019

(30) Foreign Application Priority Data

Jun. 30, 2016 (KR) .................. 10-2016-0082547

(51) Int. Cl.
*C12N 9/16* (2006.01)
*C12P 19/02* (2006.01)
(Continued)

(52) U.S. Cl.
CPC ......... *C12N 9/1205* (2013.01); *C12N 9/1051* (2013.01); *C12N 9/12* (2013.01);
(Continued)

(58) Field of Classification Search
None
See application file for complete search history.

(56) References Cited

U.S. PATENT DOCUMENTS 10,138,506 B2 * 11/2018 Wichelecki ............. C12P 19/02
2004/0126377 A1    7/2004 Meissner et al.

FOREIGN PATENT DOCUMENTS

KR    10-2014-0143109 A    12/2014
KR    10-1480422 B1    1/2015
(Continued)

OTHER PUBLICATIONS

Studer. Residue mutations and their impact on protein structure and function: detecting beneficial and pathogenic changes. Biochem. J. (2013) 449, 581-594.*

(Continued)

*Primary Examiner* — Yong D Pak
(74) *Attorney, Agent, or Firm* — Squire Patton Boggs (US) LLP (57) ABSTRACT

The present disclosure relates to tagatose-6-phosphate phosphatase consisting of an amino acid sequence of SEQ ID NO: 1, a nucleic acid encoding the tagatose-6-phosphate phosphatase, and a transformant comprising the nucleic acid. Additionally, the present disclosure relates to a composition for producing tagatose, which comprises the tagatose-6-phosphate phosphatase of the present disclosure, and
(Continued)

a method for producing tagatose using the tagatose-6-phosphate phosphatase of the present disclosure.

10 Claims, 4 Drawing Sheets

Specification includes a Sequence Listing.

(51) Int. Cl.
    *C12N 1/20*     (2006.01)
    *C12N 15/00*     (2006.01)
    *C12P 21/06*     (2006.01)
    *C12P 21/04*     (2006.01)
    *C07H 21/04*     (2006.01)
    *C12N 9/12*     (2006.01)
    *C12N 15/52*     (2006.01)
    *C12N 9/10*     (2006.01)
    *C12N 9/26*     (2006.01)
    *C12N 9/44*     (2006.01)

(52) U.S. Cl.
    CPC ........... *C12N 9/246* (2013.01); *C12N 9/2414* (2013.01); *C12N 9/2457* (2013.01); *C12N 15/52* (2013.01); *C12P 19/02* (2013.01); *C12Y 204/01007* (2013.01); *C12Y 207/01002* (2013.01); *C12Y 207/01144* (2013.01); *C12Y 302/01001* (2013.01); *C12Y 302/0101* (2013.01); *C12Y 302/01003* (2013.01); *C12Y 302/01041* (2013.01); *C12Y 302/01068* (2013.01)

(56) References Cited

FOREIGN PATENT DOCUMENTS

| KR | 10-1620904 B1 | 5/2016 |
| KR | 10-1627921 B1 | 6/2016 |
| WO | WO 03-008617 A1 | 1/2003 |

OTHER PUBLICATIONS

Database UniProtKB/TrEMBL, [online], Accession No. B9K8H1, entry version 34, dated Mar. 16, 2016, 1 page.

Kim et al., "Cloning, expression and characterization of L-arabinose isomerase from Thermotoga neapolitana: bioconversion of D-galactose to D-tagatose using the enzyme", FEMS Microbiology Letters, 2002, vol. 212, pp. 121-126.

Rodionova et al., "Diversity and Versatility of the Thermotoga maritinia Sugar Kinome", Journal of Bacteriology, Oct. 2012, vol. 194, No. 20, pp. 5552-5563.

International Search Report and Written Opinion of PCT/KR2017/006988 dated Sep. 20, 2017 together with the English translation of the International Search Report, 13 pages.

Ausubel et al., Current Protocols in Molecular Biology, John Wiley & Sons, Inc., New York, Dec. 4, 2003, from Unit 2.9A to 2.10.16; 37 pages.

NCBI, GenBank accession No. ACM23254.1, "Inositol-1-monophosphatase [Thermotoga neapolitana DSM 4359]", Jan. 30, 2014, 1 page.

NCBI, GenBank accession No. CP000916.1, "Thermotoga neapolitana DSM 4359, complete genome", Jan. 30, 2014, 2 pages.

Van Der Heiden et al., "A Pathway Closely Related to the D-tagatose Pathway of Gram-negative Enterobacteria Identified in the Gram-positive Bacterium Bacillus Licheniformis", Applied and Environmental Microbiology, Mar. 22, 2013, vol. 79, No. 11, pp. 3511-3515.

Nirakar Pradhan et al., "Hydrogen Production by the Thermophilic Bacterium Thermotoga neapolitana", Int. J. Mol. Sci., vol. 16, No. 12, Dec. 1, 2015, pp. 12578-12600, XP055652939.

* cited by examiner

SEQUENCE LISTING

<160> NUMBER OF SEQ ID NOS: 8

<210> SEQ ID NO 1
<211> LENGTH: 263

<212> TYPE: PRT
<213> ORGANISM: Artificial Sequence
<220> FEATURE:
<223> OTHER INFORMATION: Synthetic: Syntagatose-6-phosphate phosphatase

<400> SEQUENCE: 1

```
Met Glu Gly Gly Ile Glu Leu Asp Arg Leu Asp Phe Ser Ile Lys Leu
1               5                   10                  15

Leu Arg Arg Val Gly His Phe Leu Met Leu His Trp Gly Lys Val Asp
            20                  25                  30

Ser Val Glu Lys Lys Thr Gly Phe Lys Asp Ile Val Thr Glu Ile Asp
        35                  40                  45

Lys Lys Ala Gln Glu Met Ile Val Glu Ile Arg Lys Val Phe Pro
    50                  55                  60

Asp Glu Asn Ile Ile Ala Glu Glu Gly Ile Ser Glu Asn Gly Lys Lys
65                  70                  75                  80

Leu Trp Ile Ile Asp Pro Ile Asp Gly Thr Ile Asn Phe Val His Gly
                85                  90                  95

Leu Pro Asn Phe Ser Ile Ser Ile Ala Tyr Val Glu Asn Gly Glu Val
            100                 105                 110

Lys Met Gly Val Val His Ala Pro Ala Leu Asn Glu Thr Leu Tyr Ala
        115                 120                 125

Glu Glu Asn Gly Gly Ala Phe Leu Asn Gly Glu Arg Ile Arg Val Ser
    130                 135                 140

Gly Asn Thr Ser Leu Glu Glu Cys Val Gly Ser Thr Gly Ser Tyr Val
145                 150                 155                 160

Asp Phe Thr Gly Lys Phe Ile Glu Lys Met Glu Lys Lys Thr Arg Arg
                165                 170                 175

Val Arg Ile Leu Gly Ser Ala Ala Leu Asn Ala Cys Tyr Val Gly Ala
            180                 185                 190

Gly Arg Val Asp Phe Phe Val Thr Trp Arg Ile Asn Pro Trp Asp Ile
        195                 200                 205

Ala Ala Gly Leu Ile Val Val Lys Glu Ala Gly Gly Thr Val Thr Asp
    210                 215                 220

Phe Ala Gly Lys Glu Ala Asn Val Phe Ser Lys Asn Phe Val Phe Ser
225                 230                 235                 240

Asn Gly Leu Val His Glu Glu Val Leu Glu Val Val Asn Glu Val Leu
                245                 250                 255

Lys Glu Ile Gly Glu Gly Lys
                260
```

<210> SEQ ID NO 2
<211> LENGTH: 792
<212> TYPE: DNA
<213> ORGANISM: Artificial Sequence
<220> FEATURE:
<223> OTHER INFORMATION: Synthetic: tagatose-6-phosphate phosphatase

<400> SEQUENCE: 2

```
atggaggag  ggatcgaatt  ggacagactg  gactttcga   taaaactcct  gagaagggtt    60
gggcactttc  tcatgcttca  ctggggaaag  gtggacagtg  tggagaaaaa  gaccggtttc   120
aaagacatcg  tgacggaaat  agacaaaaag  gcccaggaga  tgatagtgga  ggagatcaga   180 aaggttttc   cggatgagaa  cataatagcg  gaggagggaa  tctcggagaa  cggaaaaaaa   240
ctctggataa  tagatcccat  agacgggacg  ataaacttcg  ttcatggact  tcccaacttt   300
tccatctcca  tcgcttacgt  ggagaatgga  gaggtgaaga  tgggagttgt  gcacgctcct   360
```

```
gcactcaacg aaacactcta cgccgaagaa aacggggtg ctttttttgaa cggtgaaagg    420 atcagggtgt ctggaaacac aagtcttgaa gagtgcgtgg gatcaacggg aagctatgtg    480
gatttcaccg aaagtttat cgagaagatg gaaagaaaa caaggagagt gagaattctg     540
gggagtgcgg cgctgaacgc ctgctacgtg ggagcaggga gggtggattt cttcgtcact    600
tggaggatca atccgtggga catcgcagca ggcctgatag ttgtgaaaga ggcgggagga    660
acggtgacag atttgccgg aaaagaggca acgtttct cgaagaattt tgtcttctcc      720
aacggactcg ttcacgaaga agttctcgaa gtggtgaacg aggttctgaa agagatagga    780
gaggggaagt ga                                                        792
```

<210> SEQ ID NO 3
<211> LENGTH: 28
<212> TYPE: DNA
<213> ORGANISM: Artificial Sequence
<220> FEATURE:
<223> OTHER INFORMATION: Synthetic: forward primer

<400> SEQUENCE: 3
ttttcatatg gagggaggga tcgaattg                                        28

<210> SEQ ID NO 4
<211> LENGTH: 27
<212> TYPE: DNA
<213> ORGANISM: Artificial Sequence
<220> FEATURE:
<223> OTHER INFORMATION: Synthetic: reverse primer

<400> SEQUENCE: 4
catactcgag cttcccctct cctatct                                         27

<210> SEQ ID NO 5
<211> LENGTH: 270
<212> TYPE: PRT
<213> ORGANISM: Artificial Sequence
<220> FEATURE:
<223> OTHER INFORMATION: Synthetic: polyphosphate-dependent glucokinase

<400> SEQUENCE: 5

Met Leu Ala Ala Ser Asp Ser Ser Gln His Gly Gly Lys Ala Val Thr
1               5                   10                  15

Leu Ser Pro Met Ser Val Ile Leu Gly Ile Asp Ile Gly Gly Ser Gly
            20                  25                  30

Ile Lys Gly Ala Pro Val Asp Thr Ala Thr Gly Lys Leu Val Ala Glu
        35                  40                  45

Arg His Arg Ile Pro Thr Pro Glu Gly Ala His Pro Asp Ala Val Lys
    50                  55                  60

Asp Val Val Val Glu Leu Val Arg His Phe Gly His Ala Gly Pro Val
65                  70                  75                  80

Gly Ile Thr Phe Pro Gly Ile Val Gln His Gly His Thr Leu Ser Ala
                85                  90                  95

Ala Asn Val Asp Lys Ala Trp Ile Gly Leu Asp Ala Asp Thr Leu Phe
            100                 105                 110

Thr Glu Ala Thr Gly Arg Asp Val Thr Val Ile Asn Asp Ala Asp Ala
        115                 120                 125

Ala Gly Leu Ala Glu Ala Arg Phe Gly Ala Gly Ala Gly Val Pro Gly
    130                 135                 140

Glu Val Leu Leu Leu Thr Phe Gly Thr Gly Ile Gly Ser Ala Leu Ile

```
145                 150                 155                 160

Tyr Asn Gly Val Leu Val Pro Asn Thr Glu Phe Gly His Leu Tyr Leu
                165                 170                 175

Lys Gly Asp Lys His Ala Glu Thr Trp Ala Ser Asp Arg Ala Arg Glu
            180                 185                 190

Gln Gly Asp Leu Asn Trp Lys Gln Trp Ala Lys Arg Val Ser Arg Tyr
            195                 200                 205

Leu Gln Tyr Leu Glu Gly Leu Phe Ser Pro Asp Leu Phe Ile Ile Gly
    210                 215                 220

Gly Gly Val Ser Lys Lys Ala Asp Lys Trp Gln Pro His Val Ala Thr
225                 230                 235                 240

Thr Arg Thr Arg Leu Val Pro Ala Ala Leu Gln Asn Glu Ala Gly Ile
                245                 250                 255

Val Gly Ala Ala Met Val Ala Ala Gln Arg Ser Gln Gly Asp
                260                 265                 270

<210> SEQ ID NO 6
<211> LENGTH: 253
<212> TYPE: PRT
<213> ORGANISM: Artificial Sequence
<220> FEATURE:
<223> OTHER INFORMATION: Synthetic: polyphosphate-dependent glucokinase

<400> SEQUENCE: 6

Met Gly Arg Gln Gly Met Glu Ile Leu Gly Ile Asp Ile Gly Gly Ser
1               5                   10                  15

Gly Ile Lys Gly Ala Pro Val Asp Val Glu Thr Gly Gln Leu Thr Ala
            20                  25                  30

Glu Arg Tyr Arg Leu Pro Thr Pro Glu Asn Ala Leu Pro Glu Glu Val
        35                  40                  45

Ala Leu Val Val Ala Gln Ile Val Glu His Phe Gln Trp Lys Gly Arg
    50                  55                  60

Val Gly Ala Gly Phe Pro Ala Ala Ile Lys His Gly Val Ala Gln Thr
65                  70                  75                  80

Ala Ala Asn Ile His Pro Thr Trp Ile Gly Leu His Ala Gly Asn Leu
                85                  90                  95

Phe Ser Glu Lys Cys Gly Cys Pro Val Ser Val Leu Asn Asp Ala Asp
            100                 105                 110

Ala Ala Gly Leu Ala Glu Met Ile Phe Gly Ala Gly Lys Gly Gln Lys
        115                 120                 125

Gly Val Val Leu Met Ile Thr Ile Gly Thr Gly Ile Gly Thr Ala Leu
    130                 135                 140

Phe Thr Asp Gly Ile Leu Val Pro Asn Thr Glu Leu Gly His Ile Glu
145                 150                 155                 160

Ile Arg Gly Lys Asp Ala Glu Gln Arg Ser Ser Glu Ala Ala Arg Gln
                165                 170                 175

Arg Lys Asp Trp Thr Trp Gln Gln Trp Ala Lys Arg Leu Asn Glu His
            180                 185                 190

Leu Glu Arg Leu Glu Ala Leu Phe Trp Pro Asp Leu Phe Ile Leu Gly
        195                 200                 205

Gly Gly Ala Val Lys Asn His Glu Lys Phe Phe Pro Tyr Leu Lys Leu
    210                 215                 220

Arg Thr Pro Phe Val Ala Ala Lys Leu Gly Asn Leu Ala Gly Ile Val
225                 230                 235                 240

Gly Ala Ala Trp Tyr Ala His Thr Gln Glu Thr Gln Ala
```

<210> SEQ ID NO 7
<211> LENGTH: 813
<212> TYPE: DNA
<213> ORGANISM: Artificial Sequence
<220> FEATURE:
<223> OTHER INFORMATION: Synthetic: polyphosphate-dependent glucokinase

<400> SEQUENCE: 7

```
atgctggcag ccagtgacag cagccagcat ggcgggaagg ctgttacgct atctcccatg      60
agcgtgatcc tcggattga cataggtggg agcggcatca agggggcccc tgtggacacg     120
gcaaccggga agctggtggc cgagcgccac cgcatcccca cgcccgaggg cgcgcaccca     180
gacgcggtga aggacgtggt ggttgagctg gtgcggcatt ttgggcatgc ggggccagtc     240
ggcatcactt tccctggcat cgtgcagcac ggccataccc tgagcgcagc caatgtggat     300
aaagcctgga ttggcctgga cgccgacacg cttttactg aggcgaccgg tcgcgacgtg     360
accgtgatca cgacgcaga tgccgcgggg ctagcggagg cgaggttcgg ggccggggca     420
ggtgtgccgg cgaggtgtt gctgttgacc tttgggacag gcatcggcag cgcgctgatc     480
tataacggcg tgctggtgcc caacaccgag tttgggcatc tgtatctcaa gggcgacaag     540
cacgccgaga catgggcgtc cgaccgggcc cgtgagcagg gcgacctgaa ctggaagcag     600
tgggccaaac gggtcagccg gtacctccag tatctggaag gtctcttcag tcccgatctc     660
tttatcatcg gtggggcgt gagcaagaag gccgacaagt ggcagccgca cgtcgcaaca     720
acacgtaccc gcctggtgcc cgctgccctc cagaacgagg ccggaatcgt ggggggccgcg     780
atggtggcgg cgcagcggtc acaggggac taa                                   813
```

<210> SEQ ID NO 8
<211> LENGTH: 762
<212> TYPE: DNA
<213> ORGANISM: Artificial Sequence
<220> FEATURE:
<223> OTHER INFORMATION: Synthetic: polyphosphate-dependent glucokinase

<400> SEQUENCE: 8

```
atggggaggc agggcatgga aattttaggg attgatatcg gaggatccgg catcaaaggg      60
gctccggtgg atgtagaaac cggccagtta accgccgagc gataccgctt acccaccccc     120
gaaaatgcct tacctgaaga agtggctctg tagttgccc aaattgtcga acactttcag     180
tggaaaggtc gtgtagggc aggatttcct gctgccatca agcacggcgt ggcacagacg     240
gccgcaaaca tccaccctac atggattgga cttcatgctg caacctttt cagcgaaaaa     300
tgcggatgtc ctgtctcagt gttgaatgat gcggatgctg ccggactggc ggaaatgatc     360
tttgggcag gaaaaggcca gaaaggggtg gtgctgatga ttaccattgg cactggcatc     420
gggacagccc tgttcaccga tgggatattg gtccctaata ccgagttggg acatattgaa     480
attcgggca aagatgccga acagcgctct tcggaagccg cccgccagcg gaaggattgg     540
acctggcaac aatgggcaaa gcgtctgaat gagcatttgg agcgcctgga agccctgttc     600
tggcccgatt tattcatcct tggtggaggg gcagtaaaaa atcatgaaaa gttcttccct     660
tatctaaaac tgcgtactcc cttgttgca gcaaaattgg ggaatctggc tgggattgta     720
ggcgcagcgt ggtatgctca cacccaggaa acgcaagcct ga                        762
```

THERMOSTABLE TAGATOSE-6-PHOSPHATE PHOSPHATASE AND A METHOD FOR PRODUCING TAGATOSE USING THE SAME

TECHNICAL FIELD

The present disclosure relates to tagatose-6-phosphate phosphatase and a method for producing tagatose using the same.

BACKGROUND ART

A method for producing D-tagatose from D-galactose by using L-arabinose isomerase and a method for producing tagatose from D-fructose by using L-ribulose-5-phosphate-4-epimerase have been reported as methods for producing tagatose using a conventional single enzyme conversion reaction. However, in such single enzyme conversion reaction, there is a certain level of reaction equilibrium between a substrate and a product (product/substrate=about 20% to 50%). Therefore, in the case of producing high-purity tagatose using the single enzyme conversion reaction, an additional purification process for isolating and removing a high concentration of a substrate from the reaction resultant is required.

On the other hand, for the method for producing D-tagatose using a multiple enzyme conversion reaction, a preparation method comprising producing D-fructose-6-phosphate from adenosine triphosphate (ATP) and fructose by using hexokinase (EC 2.7.1.1), converting the D-fructose-6-phosphate to D-tagatose-6-phosphate by using D-fructose-1,6-bisphosphate-aldolase (EC 4.1.2.13) having the activity of fructose-6-phosphate-4-epimerase, and producing D-tagatose from D-tagatose-6-phosphate by using a phytase as a phosphatase has already been reported (Korean Patent Nos. 10-1627921 and 10-1620904). However, the multiple enzyme reaction requires expensive ATP as a phosphate donor, and is limited in process application due to low physicochemical (heat, pH, etc.) stabilities of the adenine nucleotides AMP, ADP, and ATP. In addition, phytases induce irreversible reactions due to their variety of substrates, and thus has a limit in increasing the production yield of tagatose.

DISCLOSURE

Technical Problem

The present inventors have made extensive efforts to develop a method for producing tagatose in high yield while using economical raw materials. As a result, when tagatose-6-phosphate is produced through the conversion from sucrose, starch, or maltodextrin, which are economical raw materials, to glucose or glucose-1-phosphate, glucose-6-phosphate, and fructose-6-phosphate, it was found that tagatose can be produced with one-pot enzymatic conversions in which a plurality of enzymes involved in the tagatose production pathway can be used simultaneously, by carrying out tagatose-6-phosphate dephosphorylation as an irreversible reaction pathway using the tagatose-6-phosphate phosphatase of the present disclosure; and that the conversion rate to tagatose can be remarkably increased, thereby completing the present disclosure.

Technical Solution

An object of the present disclosure is to provide tagatose-6-phosphate phosphatase consisting of an amino acid sequence of SEQ ID NO: 1.

Another object of the present disclosure is to provide a nucleic acid encoding the tagatose-6-phosphate phosphatase of the present disclosure.

Still another object of the present disclosure is to provide a transformant comprising the nucleic acid encoding the tagatose-6-phosphate phosphatase of the present disclosure.

Still another object of the present disclosure is to provide a composition for producing tagatose, comprising the tagatose-6-phosphate phosphatase of the present disclosure, a microorganism expressing the tagatose-6-phosphate phosphatase, or a culture of the microorganism expressing the tagatose-6-phosphate phosphatase.

Still another object of the present disclosure is to provide a method for producing tagatose using the tagatose-6-phosphate phosphatase of the present disclosure.

Advantageous Effects

Since the tagatose-6-phosphate phosphatase of the present disclosure is thermostable, it can be used to industrially produce tagatose, the production of tagatose in a high concentration is possible by exploiting an irreversible reaction pathway, and tagatose can be produced with a one-pot enzymatic conversion by using sucrose, starch, or maltodextrin, which are economical raw materials, as a raw material. Therefore, since the process for producing high-purity tagatose can be simplified, the production method is advantageous in that it is both simple and economical.

BEST MODE

Hereinbelow, the present disclosure will be described in detail. Meanwhile, each of the explanations and exemplary embodiments disclosed herein can be applied to other explanations and exemplary embodiments. That is, all combinations of various factors disclosed herein belong to the scope of the present disclosure. Furthermore, the scope of the present disclosure should not be limited by the specific disclosure provided hereinbelow.

In order to achieve the object of the present disclosure, an aspect of the present disclosure provides tagatose-6-phosphate phosphatase consisting of an amino acid sequence of SEQ ID NO: 1.

The tagatose-6-phosphate phosphatase of the present disclosure may comprise a polypeptide having a homology to the amino acid sequence of SEQ ID NO: 1 of at least 80%, 90%, 95%, 97%, or 99%. For example, it is apparent that a protein having an amino acid sequence having deletion, modification, substitution, or addition of some sequences falls within the scope of the present disclosure as long as it has the homology and exhibits efficacy corresponding to that of the protein consisting of the amino acid sequence of SEQ ID NO: 1.

Additionally, as long as a protein has efficacy corresponding to that of the tagatose-6-phosphate phosphatase of the present disclosure, which consists of the amino acid sequence of SEQ ID NO: 1, it does not exclude a mutation that can occur by a meaningless sequence addition upstream or downstream of the amino acid sequence of SEQ ID NO: 1, a naturally occurring mutation, or a silent mutation. In addition, a protein including the amino acid sequence of SEQ ID NO: 1 also belongs to the scope of the present disclosure.

Further, the tagatose-6-phosphate phosphatase may be encoded by the nucleotide sequence of SED ID NO: 2, or the tagatose-6-phosphate phosphatase may be encoded by a nucleotide sequence having a homology to the nucleotide sequence of SEQ ID NO: 2 of at least 80%, 90%, 95%, 97%, or 99%, but is not limited thereto. Based on codon degeneracy, it is apparent that proteins which consist of the amino acid sequence of SEQ ID NO: 1, or polynucleotides which can be translated into proteins having a homology to the above proteins, can also be included in the scope of the present disclosure.

As used herein, the term "homology" refers to a degree of matching with a given amino acid sequence or nucleotide sequence, and the homology may be expressed as a percentage. In the present disclosure, a homology sequence having an activity which is identical or similar to the given amino acid sequence or nucleotide sequence is expressed as "% homology". The homology sequence may be determined by, for example, standard software, specifically, BLAST 2.0, which calculates the parameters such as score, identity, similarity, etc., or by comparing the sequences in a Southern hybridization experiment under defined stringent conditions, and defining appropriate hybridization conditions is within the skill of the art, and may be determined by a method well known to those skilled in the art (for example, J. Sambrook et al., Molecular Cloning, A Laboratory Manual, 2nd Edition, Cold Spring Harbor Laboratory press, Cold Spring Harbor, N.Y., 1989; F. M. Ausubel et al., Current Protocols in Molecular Biology, John Wiley & Sons, Inc., New York). As used herein, the term "stringent conditions" refers to conditions that are designed to permit specific hybridization between polynucleotides. For example, these conditions are specifically described in the literature (e.g., J. Sambrook et al., supra).

In the present disclosure, the stringent conditions may be adjusted to determine the homology. In order to confirm the homology between polynucleotides, hybridization conditions of low stringency, corresponding to a $T_m$ value of 55° C., may be used. For example, conditions of 5×SSC, 0.1% SDS, 0.25% milk, and no formamide; or 30% formamide, 5×SSC, and 0.5% SDS may be used. Hybridization conditions of mild stringency correspond to high $T_m$ values; for example, 40% formamide and 5× or 6×SSC may be used. Hybridization conditions of high stringency correspond to the highest $T_m$ values; for example, 50% formamide and 5× or 6×SSC may be used, but the hybridization conditions are not limited to the examples above.

Hybridization requires that two nucleic acids have complementary sequences, although mismatches between bases are possible depending on the stringency of hybridization. The term "complementary" is used to describe the relationship between nucleotide bases that are capable of being hybridized with each other. For example, with respect to DNA, adenosine is complementary to thymine and cytosine is complementary to guanine. Therefore, the present disclosure may also include substantially similar nucleic acid sequences as well as isolated nucleic acid fragments complementary to the entire sequence.

Specifically, the polynucleotide having homology can be detected using hybridization conditions including a hybridization step at a $T_m$ value of 55° C. and using the above-described conditions. In addition, the $T_m$ value may be 60° C., 63° C., or 65° C., but is not limited thereto. Those skilled in the art can appropriately adjust the $T_m$ value according to its purpose.

The appropriate stringency of hybridizing the polynucleotides is dependent on the length and degree of complementarity of the polynucleotides, and the variables are well known in the art. As the similarity or homology between the two nucleotides becomes greater, the $T_m$ value for hybrids of the polynucleotides having such sequence becomes greater. The relative stability for the hybridization of the polynucleotides (corresponding to a higher $T_m$ value) decreases in the following order: RNA:RNA, DNA:RNA, DNA:DNA. The calculation formula of the $T_m$ values for hybrids, the length of which is greater than 100 nucleotides, is published in the art (Sambrook et al., supra, 9.50-9.51). For hybridization with shorter polynucleotides, e.g., oligonucleotides, the mismatch position may be more important, and the length of the oligonucleotides may determine the specificity thereof (Sambrook et al., supra, 11.7-11.8).

Specifically, the polynucleotides may be detected using the following hybridization conditions: 1) a hybridization step with a salt concentration lower than 500 mM and a temperature of at least 37° C.; and a washing step at at least 63° C. with 2×SSPE; 2) a hybridization step with a salt concentration lower than 200 mM and a temperature of at least 37° C.; or 3) both hybridization and washing steps at 63° C. with 2×SSPE.

The length of the hybridization nucleic acid can be, for example, at least about 10 nucleotides, 15 nucleotides, 20 nucleotides, or at least 30 nucleotides. In addition, those skilled in the art can adjust the temperature and the washing solution salt concentration as needed depending on factors such as the length of the probe.

The tagatose-6-phosphate phosphatase of the present disclosure may be an enzyme derived from *Thermotoga* sp., and specifically may be an enzyme derived from *Thermotoga* neapolitana, but is not limited thereto.

Another aspect of the present disclosure provides a nucleic acid encoding the tagatose-6-phosphate phosphatase of the present disclosure.

Still another aspect of the present disclosure provides a transformant comprising the nucleic acid encoding the tagatose-6-phosphate phosphatase of the present disclosure.

As used herein, the term "transformation" refers to a process of introducing into a host cell a vector including a nucleic acid encoding a target protein, thereby enabling the expression of the protein encoded by the nucleic acid in the host cell. For the transformed nucleic acid, it does not matter whether the transformed nucleic acid is inserted into the chromosome of a host cell and located therein or located outside the chromosome, as long as it can be expressed in the host cell, and both cases are included. Additionally, the nucleic acid includes DNA and RNA which encode the target protein. The nucleic acid may be inserted in any form as long as it can be introduced into a host cell and expressed therein. For example, the nucleic acid may be introduced into a host cell in the form of an expression cassette, which is a gene construct including all essential elements required for self-expression. The expression cassette may conventionally include a promoter operably linked to the nucleic acid, a transcription termination signal, a ribosome-binding domain, and a translation termination signal. The expression cassette may be in the form of an expression vector capable of self-replication. Additionally, the nucleic acid may be introduced into a host cell as it is and operably linked to a sequence essential for its expression in the host cell, but the nucleic acid is not limited thereto.

Additionally, as used herein, the term "operably linked" refers to a functional linkage between a promoter sequence, which initiates and mediates the transcription of the nucleic acid encoding the target protein of the present disclosure, and the above gene sequence.

The method of the present disclosure for transforming the vector includes any method of introducing a nucleic acid into a cell, and may be carried out by selecting a suitable standard technique known in the art according to a host cell. Examples of the method may include electroporation, calcium phosphate ($CaPO_4$) precipitation, calcium chloride ($CaCl_2$) precipitation, microinjection, a polyethyleneglycol (PEG) technique, a DEAE-dextran technique, a cationic liposome technique, a lithium acetate-DMSO technique, etc., but are not limited thereto.

As the host cell, it is preferable to use a host having a high efficiency of introducing DNA and a high efficiency of expressing the introduced DNA. For example, it may be *E. coli*, but is not limited thereto.

Still another aspect of the present disclosure provides a composition for producing tagatose, comprising the tagatose-6-phosphate phosphatase of the present disclosure, a microorganism expressing the tagatose-6-phosphate phosphatase, or a culture of the microorganism expressing the tagatose-6-phosphate phosphatase.

Figure 1:
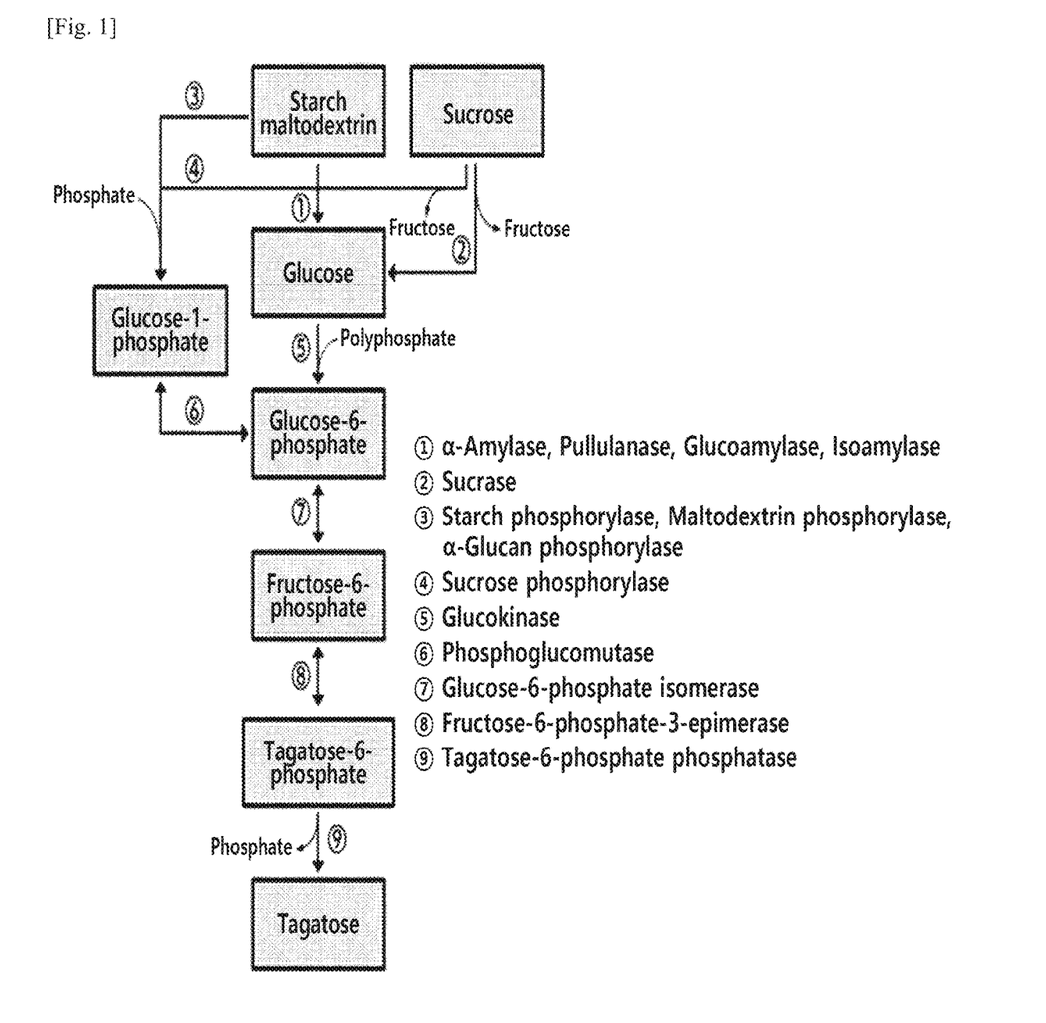
FIG. 1 schematically shows the reaction pathway capable of producing tagatose from starch (e.g., maltodextrin), sucrose, or glucose, and exhibits the enzymes involved therein.

The composition for producing tagatose may further comprise an enzyme involved in the tagatose-producing pathway (see FIG. 1) of the present disclosure, a microorganism expressing the enzyme involved in the tagatose-producing pathway of the present disclosure, or a culture of the microorganism expressing the enzyme involved in the tagatose-producing pathway of the present disclosure. However, this is merely an example; that is, an enzyme to be contained in the composition of the present disclosure for producing tagatose and a substrate used for the production of tagatose are not limited, as long as tagatose can be produced by using the tagatose-6-phosphate phosphatase of the present disclosure.

The composition of the present disclosure for producing tagatose may further comprise: (a) (i) starch, maltodextrin, sucrose, or a combination thereof, glucose, glucose-1-phosphate, glucose-6-phosphate, fructose-6-phosphate, or tagatose-6-phosphate; (ii) phosphate; (iii) fructose-6-phosphate-4-epimerase; (iv) glucose-6-phosphate isomerase; (v) phosphoglucomutase or glucokinase; and/or (vi) α-glucanophosphorylase, starch phosphorylase, maltodextrin phosphorylase or sucrose phosphorylase, or α-amylase, pullulanase, isoamylase, glucoamylase, or sucrase; or (b) a microorganism expressing any of the enzymes or a culture of the microorganism, but is not limited thereto.

The starch/maltodextrin phosphorylase (EC 2.4.1.1) and α-glucanophosphorylase of the present disclosure may include any proteins as long as these are proteins that are subjected to phosphoryl transfer from phosphate to glucose, thereby having the activity of producing glucose-1-phosphate from starch or maltodextrin. The sucrose phosphorylase (EC 2.4.1.7) of the present disclosure may include any protein as long as it is a protein that is subjected to phosphoryl transfer from phosphate to glucose, thereby having the activity of producing glucose-1-phosphate from sucrose. The α-amylase (EC 3.2.1.1), pullulanase (EC 3.2.1.41), glucoamylase (EC 3.2.1.3), and isoamylase of the present disclosure, which are enzymes for starch saccharification, may include any proteins as long as these are proteins having the activity of converting starch or maltodextrin to glucose. The sucrase (EC 3.2.1.26) of the present disclosure may include any protein as long as it s a protein having the activity of converting sucrose to glucose. The phosphoglucomutase (EC 5.4.2.2) of the present disclosure may include any protein as long as it is a protein having the activity of converting glucose-1-phosphate to glucose-6-phosphate. The glucokinase may include any protein as long as it is a protein capable of transferring phosphate to glucose, thereby having the activity of converting to glucose-6-phosphate. Specifically, the glucokinase may be a polyphosphate-dependent glucokinase, and more specifically may be a polyphosphate-dependent glucokinase derived from *Deinococcus geothermalis* consisting of the amino acid sequence of SEQ ID NO: 5 and the nucleotide sequence of SEQ ID NO: 7, or may be a polyphosphate-dependent glucokinase derived from *Anaerolinea thermophila* consisting of the amino acid sequence of SEQ ID NO: 6 and the nucleotide sequence of SEQ ID NO: 8. The glucose-6-phosphate isomerase of the present disclosure may include any protein as long as it is a protein having an activity of converting glucose-6-phosphate to fructose-6-phosphate. The fructose-6-phosphate-4-epimerase of the present disclosure may include any protein as long as it is a protein having an activity of converting fructose-6-phosphate to tagatose-6-phosphate.

The composition of the present disclosure for producing tagatose may further comprise an ion or salt of a metal selected from the group consisting of Mg, Mn, and Zn. Specifically, the metal salt of the present disclosure may be a salt of a metal selected from the group consisting of $MgCl_2$, $MgSO_4$, $MnCl_2$, $MnSO_4$, $ZnCl_2$, and $ZnSO_4$.

Still another aspect of the present disclosure provides a method for producing tagatose, comprising converting tagatose-6-phosphate to tagatose by reacting the tagatose-6-phosphate with the tagatose-6-phosphate phosphatase of the present disclosure, a microorganism expressing the tagatose-6-phosphate phosphatase, or a culture of the microorganism expressing the tagatose-6-phosphate phosphatase.

The production method of the present disclosure may further comprise converting fructose-6-phosphate to tagatose-6-phosphate by reacting the fructose-6-phosphate with fructose-6-phosphate-4-epimerase, a microorganism expressing the fructose-6-phosphate-4-epimerase, or a culture of the microorganism expressing the fructose-6-phosphate-4-epimerase, prior to converting the tagatose-6-phosphate to tagatose.

Additionally, the production method may further comprise converting glucose-6-phosphate to fructose-6-phosphate by reacting the glucose-6-phosphate with glucose-6-phosphate isomerase, a microorganism expressing the glucose-6-phosphate isomerase, or a culture of the microorganism expressing the glucose-6-phosphate isomerase, prior to converting the fructose-6-phosphate of the present disclosure to tagatose-6-phosphate.

Additionally, the production method may further comprise converting glucose-1-phosphate to glucose-6-phosphate by reacting the glucose-1-phosphate with phosphoglucomutase, a microorganism expressing the phosphoglucomutase, or a culture of the microorganism expressing the phosphoglucomutase, prior to converting the glucose-6-phosphate of the present disclosure to fructose-6-phosphate.

Additionally, the production method may further comprise converting glucose to glucose-6-phosphate by reacting the glucose with glucokinase, a microorganism expressing the glucokinase, or a culture of the microorganism expressing the glucokinase, and phosphate, prior to converting the glucose-6-phosphate of the present disclosure to fructose-6-phosphate.

Additionally, the production method may further comprise converting starch, maltodextrin, sucrose, or a combination thereof to glucose-1-phosphate by reacting the starch, maltodextrin, sucrose, or combination thereof with phosphate and α-glucanophosphorylase, starch phosphorylase, maltodextrin phosphorylase, or sucrose phosphorylase; a microorganism expressing the α-glucanophosphorylase, starch phosphorylase, maltodextrin phosphorylase, or sucrose phosphorylase; or a culture of the microorganism expressing the α-glucanophosphorylase, starch phosphorylase, maltodextrin phosphorylase, or sucrose phosphorylase, prior to converting the glucose-1-phosphate of the present disclosure to glucose-6-phosphate.

Additionally, the production method may further comprise converting starch, maltodextrin, sucrose, or a combination thereof to glucose by reacting the starch, maltodextrin, sucrose, or combination thereof with α-amylase, pullulanase, glucoamylase, sucrase, or isoamylase; a microorganism expressing the α-amylase, pullulanase, glucoamylase, sucrase, or isoamylase; or a culture of the microorganism expressing the α-amylase, pullulanase, glucoamylase, sucrase, or isoamylase, prior to converting the glucose of the present disclosure to glucose-6-phosphate.

The production method may further comprise converting glucose to starch, maltodextrin, or sucrose by reacting the glucose with 4-α-glucanotransferase, a microorganism expressing the 4-α-glucanotransferase, or a culture of the microorganism expressing the 4-α-glucanotransferase.

In the production method, the "reaction" may be carried out at a pH of 5.0 to 8.0, a temperature of 60° C. to 90° C., and/or for 1 minute to 24 hours. Specifically, the reaction of the present disclosure may be carried out at a pH of 6.0 to 8.0, a pH of 6.5 to 8.0, or a pH of 6.5 to 7.5. Additionally, the reaction of the present disclosure may be carried out at 60° C. to 90° C., 70° C. to 90° C. or 75° C. to 85° C. Further, the reaction of the present disclosure may be carried out for 1 minute to 12 hours, 1 minute to 6 hours, 1 minute to 3 hours, 1 minute to 1 hour, 5 minutes to 24 hours, 5 minutes to 12 hours, 5 minutes to 6 hours, 5 minutes to 3 hours, 5 minutes to 1 hour, 10 minutes to 24 hours, 10 minutes to 12 hours, 10 minutes to 6 hours, 10 minutes to 3 hours, or 10 minutes to 1 hour.

Additionally, the reaction of the present disclosure may be carried out in the presence of an ion or salt of a metal selected from the group consisting of Mg, Mn, and Zn. Specifically, the metal salt of the present disclosure may be a salt of a metal selected from the group consisting of $MgCl_2$, $MgSO_4$, $MnCl_2$, $MnSO_4$, $ZnCl_2$, and $ZnSO_4$.

Still another aspect of the present disclosure provides a method for producing tagatose, comprising reacting starch, maltodextrin, sucrose, or a combination thereof, and phosphate with (a) tagatose-6-phosphate phosphatase; fructose-6-phosphate-4-epimerase; glucose-6-phosphate isomerase: phosphoglucomutase or glucokinase; and α-glucanophosphorylase, starch phosphorylase, maltodextrin phosphorylase, sucrose phosphorylase, α-amylase, pullulanase, isoamylase, glucoamylase, or sucrase; or (b) a microorganism expressing any of the enzymes or a culture of the microorganism.

MODE FOR INVENTION

Hereinbelow, the present disclosure will be described in detail with accompanying exemplary embodiments. However, the exemplary embodiments disclosed herein are only for illustrative purposes and should not be construed as limiting the scope of the present disclosure.

Example 1: Preparation of Recombinant Expression Vector Containing Gene of Tagatose-6-Phosphate Phosphatase, and Transformed Microorganism In order to discover novel thermostable D-tagatose-6-phosphate phosphatase, a gene was isolated from *Thermotoga neapolitana*, a thermophilic microorganism, and then a recombinant expression vector and a transformed microorganism were produced.

Specifically, based on gene sequences of *Thermotoga neapolitana* registered in Genbank, t6pp, which is a gene expected to encode tagatose-6-phosphate phosphatase, was selected. Thereafter, based on the information of its amino acid sequence (SEQ ID NO: 1) and nucleotide sequence (SEQ ID NO: 2), a forward primer (SEQ ID NO: 3) and a reverse primer (SEQ ID NO: 4) were devised and synthesized. Polymerase chain reaction (PCR) was carried out with the synthesized primers using *Thermotoga neapolitana* chromosomal DNA (genomic DNA) as a template. Specifically, PCR was carried out for a total of 25 cycles under the following conditions: denaturation at 95° C. for 30 seconds, annealing at 55° C. for 30 seconds, and polymerization at 68° C. for 2 minutes. The resultants were inserted into pET21a (Novagen Inc.), which is a plasmid vector for expression in *E. coli*, using restriction enzymes NdeI and XhoI, and then a recombinant expression vector was constructed and named as pET21a-CJ_tn_t6pp. pET21a-CJ_tn_t6pp was transformed into the *E. coli* strain BL21 (DE3) by a conventional transformation method (Sambrook et al. 1989) to prepare a microorganism transformed to a recombinant vector including the nucleotide sequence of SEQ ID NO: 2, and this was designated as *E. coli* BL21 (DE3)/CJ_tn_t6pp.

The strain *E. coli* BL21(DE3)/CJ_tn_t6pp was deposited to the Korean Culture Center of Microorganisms (KCCM), which is an international depositary authority under the Budapest Treaty, on Jun. 23, 2016, and assigned Accession No. KCCM11850P.

Example 2: Preparation of Recombinant Enzyme

In order to prepare a recombinant tagatose phosphatase (hereinafter referred to as T6PP), *E. coli* BL21 (DE3)/CJ_tn_t6pp was inoculated into a culture tube containing 5 mL of LB liquid medium, and then a seed culture was initiated in a shaking incubator at 37° C. until the absorbance at 600 nm reached 2.0. The seed culture solution was inoculated into a culture flask containing the LB liquid medium, and the main culture was carried out. When the absorbance at 600 nm reached 2.0, 1 mM IPTG was added to induce expression/production of T6PP. The seed culture and main culture were carried out at a stirring rate of 200 rpm at a temperature of 37° C. Upon completion of the main culture, the culture solution was centrifuged at 4° C. at 8,000× g for 20 minutes, and then cells were recovered. The recovered cells were washed twice with a 50 mM Tris-HCl buffer (pH 7.0), suspended in the same buffer, and then the cells were disrupted using an ultrasonic cell disruptor. The cell debris was centrifuged at 4° C. at 13,000× g for 20 minutes, and then only the supernatant was obtained. T6PP was purified from the supernatant using His-tag affinity chromatography.

Figure 2:
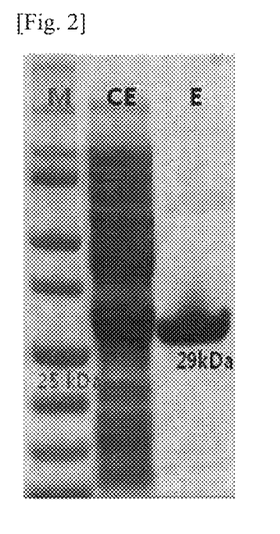
FIG. 2 shows the results of analysis of the molecular weight of the tagatose-6-phosphate phosphatase (E: T6PP) of the present disclosure by protein electrophoresis (SDS-PAGE). "M" represents a protein size marker, and "CE" represents a supernatant after transformant disruption.

The molecular weight was confirmed by SDS-PAGE analysis, and as a result, it was found that the molecular weight of the purified T6PP was about 29 kDa (indicated as "E" in FIG. 2a).

Example 3: Confirmation of Conversion Activity of T6PP to Tagatose

In order to analyze the conversion activity of T6PP from tagatose-6-phosphate to tagatose, tagatose-6-phosphate (50 mM) was suspended in a 50 mM Tris-HCl buffer (pH 7.5), and the purified T6PP (0.1 unit/mL) and $MgCl_2$ (10 mM) were added thereto. Thereafter, the resultants were reacted at 70° C. for 10 minutes, and then the reaction resultants were analyzed with HPLC. HPLC analysis was carried out using an HPX-87H column (Bio-Rad, Inc.) while flowing 5 mM sulfuric acid in the mobile phase at a flow rate of 0.6 mL/min at 60° C. Tagatose and tagatose-6-phosphate were detected by a Refractive Index Detector.

Figure 3:
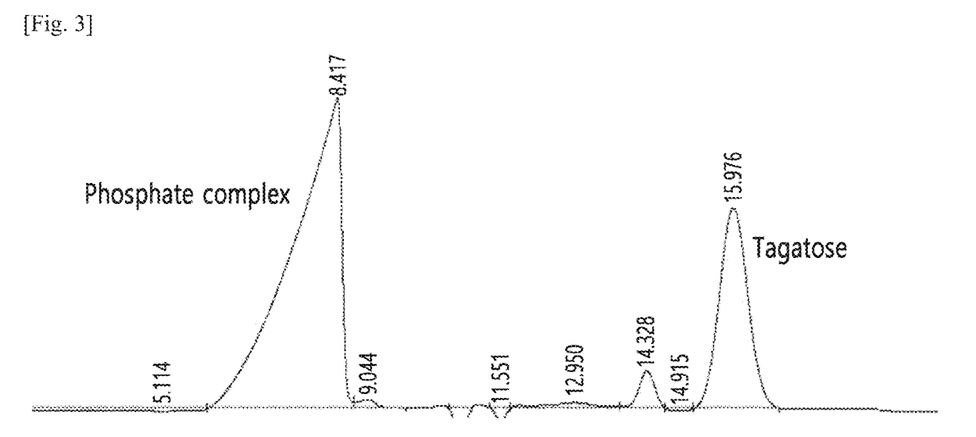
FIG. 3 is a graph showing the conversion activity of the tagatose-6-phosphate phosphatase of the present disclosure from tagatose-6-phosphate to tagatose.

As a result, it was found that tagatose was produced from the reaction product of T6PP (FIG. 3).

Example 4: Confirmation of Activity of T6PP According to pH, Temperature, and Addition of Metal Ion 4-1. Confirmation of Activity According to pH In order to investigate the influence of pH on T6PP, the purified T6PP (0.1 unit/mL) was added to tagatose-6-phosphate (50 mM) suspended in a 50 mM buffer with various pHs (pH 4.0 to 7.0, sodium citrate; pH 4.0 to 7.0, sodium acetate; pH 6.0 to 8.0, potassium phosphate: pH 7.0 to 9.0, Tris-HCl), and then reacted at 70° C. for 10 minutes. Thereafter, tagatose was quantitatively analyzed by HPLC under the same analytical conditions as in Example 3.

Figure 4:
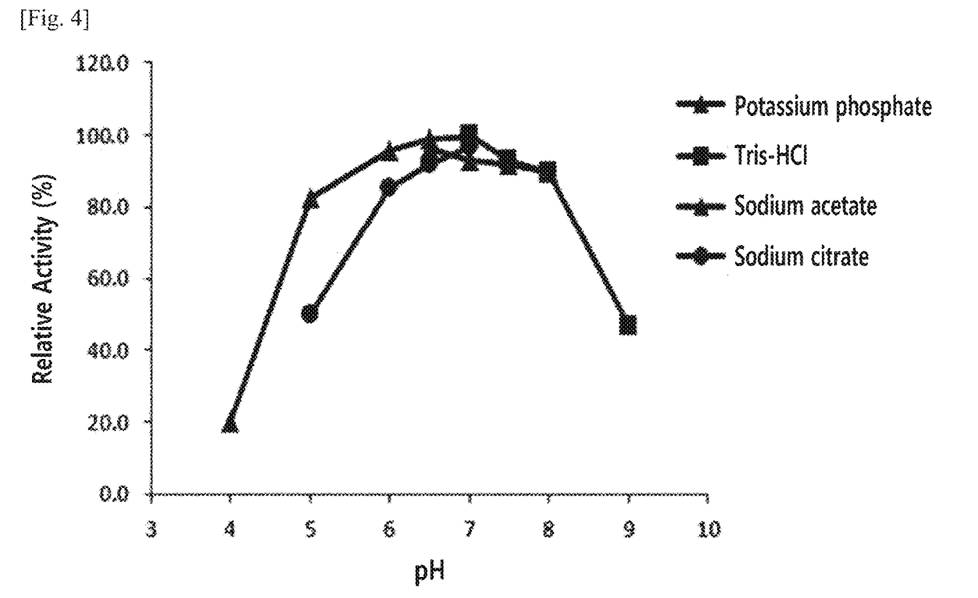
FIG. 4 is a graph showing the activity of the tagatose-6-phosphate phosphatase of the present disclosure according to the buffer solution and pH range.

As a result, it was confirmed that T6PP showed the maximum activity in the Tris-HCl buffer (especially at pH 7.0), and that T6PP showed 80% or higher of its activity at a very broad pH range (5.0 to 8.0) compared to the maximum activity (FIG. 4).

4-2. Confirmation of Activity According to Temperature

In order to analyze the activity of T6PP according to temperature, the purified T6PP (0.1 unit/mL) was added to tagatose-6-phosphate (50 mM) suspended in a 50 mM Tris-HCl buffer (pH 7.0), and then reacted at 40° C., 50° C., 60° C., 70° C., 80° C., and 90° C. for 10 minutes. Thereafter, tagatose was quantitatively analyzed by HPLC under the same analytical conditions as in Example 3.

Figure 5:
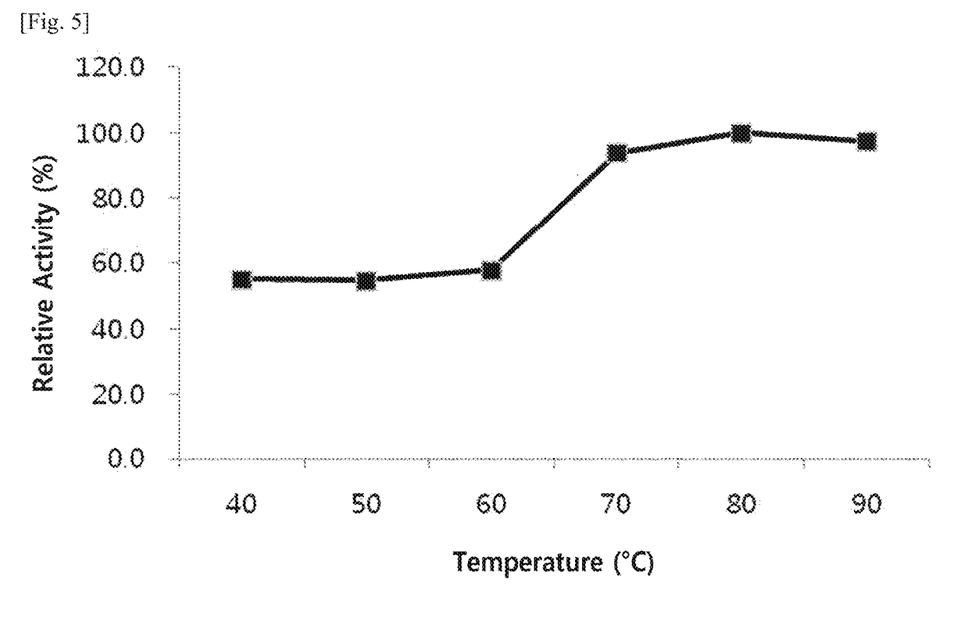
FIG. 5 is a graph showing the activity of the tagatose-6-phosphate phosphatase of the present disclosure according to the temperature.

As a result, it was confirmed that T6PP showed a high activity at 70° C. to 90° C., and particularly exhibited the maximum activity at 80° C. (FIG. 5).

4-3. Confirmation of Activity According to Addition of Metal Ion

In order to investigate the effect of addition of a metal ion on the activity of T6PP, each of the metal ions (e.g., $NiSO_4$, $CuSO_4$, $MnSO_4$, $CaCl_2$, $ZnSO_4$, $MgCl_2$, $CoSO_4$, and APO) was added to tagatose-6-phosphate (50 mM) suspended in a 50 mM Tris-HCl buffer (pH 7.0) to a final concentration of 0.5 mM. For the removal of the metal ions, T6PP (0.1 unit/mL), which was dialyzed by treating with 10 mM EDTA, was added thereto, and then the resultants were reacted at 70° C. for 10 minutes. Thereafter, tagatose was quantitatively analyzed by HPLC under the same analytical conditions as in Example 3.

Figure 6:
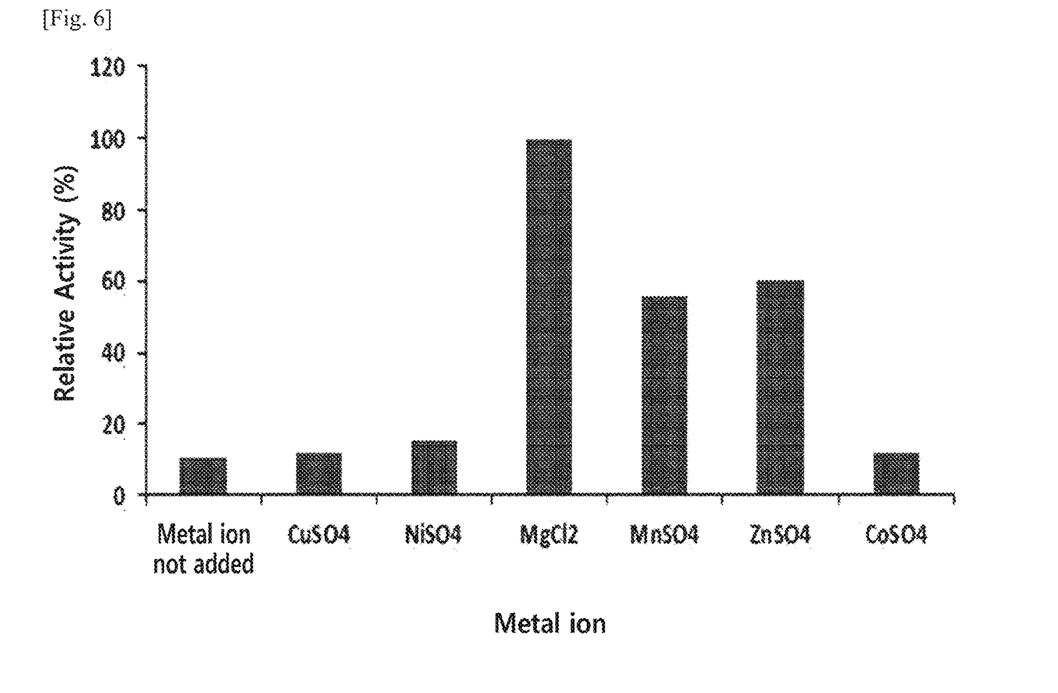
FIG. 6 is a graph showing the activity of the tagatose-6-phosphate phosphatase of the present disclosure upon addition of a metal ion.

As a result, it was confirmed that the activity of T6PP was mostly increased upon the addition of Mg ion, and that the activity was also increased upon the addition of Mn and Zn ions (FIG. 6).

Example 5: Analysis of Substrate Specificity of T6PP

In order to determine whether T6PP has substrate specificity to tagatose-6-phosphate, the activity of T6PP on various phosphorylated saccharides was analyzed. Each of glucose-1-phosphate (50 mM), glucose-6-phosphate (50 mM), fructose-6-phosphate (50 mM), tagatose-6-phosphate (50 mM), and tagatose-6-phosphate (50 mM) was used as the substrate. A 50 mM Tris-HCl buffer (pH 7.0) and the purified T6PP (1 unit/mL) were added, and then the resultants were reacted at 70° C. for 1 hour. Thereafter, each of saccharides and phosphorylated saccharides was quantitatively analyzed by HPLC under the same analytical conditions as in Example 3.

Figure 7:
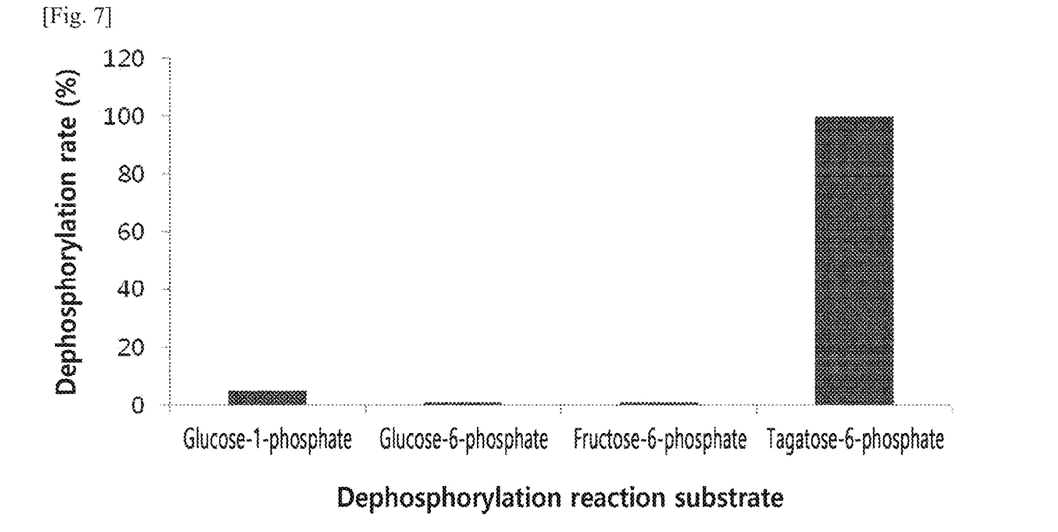
FIG. 7 is a graph showing the substrate specificity of the tagatose-6-phosphate phosphatase of the present disclosure to tagatose-6-phosphate.

As a result, it was confirmed that T6PP had a dephosphorylation activity only for tagatose-6-phosphate (FIG. 7).

While the present disclosure has been described with reference to the particular illustrative embodiments, it will be understood by those skilled in the art to which the present disclosure pertains that the present disclosure may be embodied in other specific forms without departing from the technical spirit or essential characteristics of the present disclosure. Therefore, the embodiments described above are considered to be illustrative in all respects and not restrictive. Furthermore, the scope of the present disclosure is defined by the appended claims rather than the detailed description, and it should be understood that all modifications or variations derived from the meanings and scope of the present disclosure and equivalents thereof are included in the scope of the appended claims.

The invention claimed is:

1. A method for producing tagatose, comprising: converting tagatose-6-phosphate to tagatose by reacting the tagatose-6-phosphate with a polypeptide having the amino acid sequence of SEQ ID NO: 1 and having tagatose-6-phosphate phosphatase activity, a microorganism expressing the same, or a culture of the microorganism.

2. The method according to claim 1, wherein the method further comprises converting fructose-6-phosphate to tagatose-6-phosphate by reacting the fructose-6-phosphate with fructose-6-phosphate-4-epimerase, a microorganism expressing the same, or a culture of the microorganism, prior to converting the tagatose-6-phosphate to tagatose.

3. The method according to claim 2, wherein the method further comprises converting glucose-6-phosphate to fructose-6-phosphate by reacting the glucose-6-phosphate with glucose-6-phosphate isomerase, a microorganism expressing the same, or a culture of the microorganism, prior to converting the fructose-6-phosphate to tagatose-6-phosphate.

4. The method according to claim 3, wherein the method further comprises converting glucose-1-phosphate to glucose-6-phosphate by reacting the glucose-1-phosphate with phosphoglucomutase, a microorganism expressing the same, or a culture of the microorganism, prior to converting the glucose-6-phosphate to fructose-6-phosphate.

5. The method according to claim 3, wherein the method further comprises converting glucose to glucose-6-phosphate by reacting the glucose with glucokinase, a microorganism expressing the same, or a culture of the microorganism, and phosphate, prior to converting the glucose-6-phosphate to fructose-6-phosphate.

6. The method according to claim 4, wherein the method further comprises converting starch, maltodextrin, sucrose, or a combination thereof to glucose-1-phosphate by reacting the starch, maltodextrin, sucrose, or combination thereof with phosphate and α-glucanophosphorylase, starch phosphorylase, maltodextrin phosphorylase, or sucrose phosphorylase; a microorganism expressing the same; or a culture of the microorganism, prior to converting the glucose-1-phosphate to glucose-6-phosphate.

7. The method according to claim 5, wherein the method further comprises converting starch, maltodextrin, sucrose, or a combination thereof to glucose by reacting the starch, maltodextrin, sucrose, or combination thereof with α-amylase, pullulanase, glucoamylase, sucrase, or isoamylase; a microorganism expressing the same; or a culture of the microorganism, prior to converting the glucose to glucose-6-phosphate.

8. The method according to claim 1, wherein the reaction is carried out at a pH of 5.0 to 8.0, a temperature of 60° C. to 90° C., and/or for 1 minute to 24 hours.

9. The method according to claim 1, wherein the reaction is carried out in the presence of an ion or salt of a metal selected from the group consisting of Mg, Mn, and Zn.

10. A method for producing tagatose, comprising reacting starch,
maltodextrin, sucrose, or a combination thereof, and phosphate with (a) a polypeptide having the amino acid sequence of SEQ ID NO: 1 and having tagatose-6-phosphate phosphatase activity; fructose-6-phosphate-4-epimerase; glucose-6-phosphate isomerase; phosphoglucomutase or glucokinase; and α-glucanophosphorylase, starch phosphorylase, maltodextrin phosphorylase, sucrose phosphorylase, α-amylase, pullulanase, isoamylase, glucoamylase, or sucrase; or (b) a microorganism expressing any of the enzymes or a culture of the microorganism.

* * * * *